United States Patent [19]

Kim et al.

[11] Patent Number: 5,629,154
[45] Date of Patent: May 13, 1997

[54] TELOMERASE ACTIVITY ASSAYS

[75] Inventors: Nam W. Kim, Santa Clara; Calvin B. Harley, Palo Alto; Scott L. Weinrich, San Francisco, all of Calif.

[73] Assignee: Geron Corporation, Menlo Park, Calif.

[21] Appl. No.: 315,214

[22] Filed: Sep. 28, 1994

Related U.S. Application Data

[63] Continuation-in-part of Ser. No. 255,774, Jun. 7, 1994, which is a continuation-in-part of Ser. No. 151,477, Nov. 12, 1993, which is a continuation-in-part of Ser. No. 153,051, Nov. 12, 1993.

[51] Int. Cl.$^6$ ............... C12Q 1/68; C12P 19/34; C07H 21/04; C12N 11/00
[52] U.S. Cl. ............... 435/6; 435/91.2; 435/174; 536/24.3; 536/24.33; 536/23.1; 424/94.1
[58] Field of Search ............... 435/6, 91.2, 174; 536/24.33, 23.1; 424/94.1

[56] References Cited

U.S. PATENT DOCUMENTS

| | | | |
|---|---|---|---|
| 4,424,279 | 1/1984 | Bohn et al. | 436/534 |
| 5,188,963 | 2/1993 | Stapleton | 435/299 |
| 5,231,015 | 7/1993 | Cummins et al. | 435/91 |
| 5,310,652 | 5/1994 | Gelfand et al. | 435/6 |
| 5,334,499 | 8/1994 | Burdick et al. | 435/6 |
| 5,413,924 | 5/1995 | Kosak et al. | 435/177 |
| 5,489,508 | 2/1996 | West et al. | 935/6 |

FOREIGN PATENT DOCUMENTS 9408053  4/1994  WIPO.

OTHER PUBLICATIONS

Baird et al. (1995), "Mechanims underlying telomere repeat turnover, revealed by hypervariable variant repeat distribution patterns in the human Xp/Yp telomere," EMBO J. 14:5433–5443.

Ijdo et al. (1991), "Improved telomere detection using a telomere repeat probe (TTAGGG)$_n$ generated by PCR," Nucl. Acids Res. 19:4780.

Weber et al. (1990), "Characterization and organization of DNA sequences adjacent to the human telomere associated repeat (TTAGGG)$_n$," Nucl. Acids Res. 18:3353–3361.

Wilkie et al. (1990), "A truncated human chromosome 16 associated with alpha thalassaemia is stabilized by addition of telomeric repeat (TTAGGG)$_n$," Abstract, Nature 346(6287):868–71.

Morin, Nature 353: 454–456 1991.

Barany, PNAS 88:189–193 1991.

Allsopp et al., "Telomere length predicts replicative capacity of human fibroblasts," Proc. Natl. Acad. Sci. USA 89:10114–10118 (1992).

Cotten, "The in vivo application of ribozymes," Trends in Biotechnology 8:174–178 (1990).

Counter et al., "Stabilization of Short Telomeres and Telomerase Activity Accompany Immortalization of Epstein–Barr Virus–Transformed Human B Lymphocytes," J. Virology 68:3410–3414 (1994).

Counter et al., "Telomerase activity in human ovarian carcinoma," Proc. Natl. Acad. Sci. USA 91:2900–2904 (1994).

Greider and Blackburn, "A telomeric sequence in the RNA of Tetrahymena telomerase required for telomere repeat synthesis," Nature 337:331–337 (1989).

Harley et al., "The Telomere hypothesis of Cellular Aging," Expermiental Gerontology 27:375–382 (1992).

Klingelhutz et al., "Restoration of Telomeres in Human Papoillomavirus–Immortalized Human Anogenital Epithelial Cells," Molecular and Cellular Biology 14:961–969 (1994).

(List continued on next page.)

Primary Examiner—Stephanie W. Zitomer
Assistant Examiner—Dianne Rees
Attorney, Agent, or Firm—Kevin Kaster; Richard J. Warburg; Amy S. Hellenkamp

[57] ABSTRACT

Telomerase activity in a sample can be measured using a two reaction protocol involving telomerase substrate and primer extension steps.

23 Claims, 5 Drawing Sheets

OTHER PUBLICATIONS

Shay et al., "Loss of telomeric DNA during aging may predipose cells to cancer (Review)," *Int'l J. Oncology* 3:559–563 (1993).

Strahl and Blackburn, "The effects of nucleoside analogs on telomerase and telomeres in *Tetrahymena*," *Nucleic Acids Research* 22:893–900 (1994).

Windle and McGuire, "Telomeres: the long and the short of it," *Proceedings of the American Association for Cancer Research* 33:594–595 (1992).

TS TELOMRASE PRODUCT

```
         TS                    TELOMERIC REPEATS
5'-AATCCGTCGAGCAGAGTT ag ggttag ggttag ggttag-3'
                   || || |||*|| |||*|| |||*||
   — — — — — — 3'-AA TC CCATTC CCATTC CCATTCCC-5'
                                         CX (SEQ ID NO. 2)
5'-AATCCGTCGAGCAGAGTT-3' — — — — — — — — →

TS (SEQ ID NO. 1)
```

TRAP BUFFER
dNTPs
TS OLIGONUCLEOTIDE
TAQ POLYMERASE
CELL/TISSUE EXTRACT — WAX BARRIER

LYOPHILIZED CX PRIMER

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 1:

AATCCGTCGA GCAGAGTT                                                  18

( 2 ) INFORMATION FOR SEQ ID NO: 2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear
            52-B ( i i ) SEQUENCE DESCRIPTION: SEQ ID NO: 2:

CCCTTACCCT TACCCTTACC CTAA                                    24

( 2 ) INFORMATION FOR SEQ ID NO: 3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 3:

GCGCGGCTAA CCCTAACCCT AACC                                    24

( 2 ) INFORMATION FOR SEQ ID NO: 4:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 4:

CCCAATCCGT CGAGCAGAGT TAG                        23

( 2 ) INFORMATION FOR SEQ ID NO: 5:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 5:

TAACTCTGCT CGACGGATTC CC                         22

( 2 ) INFORMATION FOR SEQ ID NO: 6:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 6:

GGGTAACCCT AACCCTAACC C                          21

( 2 ) INFORMATION FOR SEQ ID NO: 7:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 7:

GGTTAGGGTT AGGGTTAAA                             19

( 2 ) INFORMATION FOR SEQ ID NO: 8:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 8:

GTTAGGGTTA GGGTTAGG                              18

( 2 ) INFORMATION FOR SEQ ID NO: 9:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 9:

TTAGGGTTAG GGTTAGGG                              18

( 2 ) INFORMATION FOR SEQ ID NO: 10:

( i ) SEQUENCE CHARACTERISTICS:

```
        ( A ) LENGTH: 18 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 10:

CCCTAACCCT AACCCTAA                                                                    18

( 2 ) INFORMATION FOR SEQ ID NO: 11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 11:

CCCTAACCCT AACCCTAACC CTAA                                                             24

( 2 ) INFORMATION FOR SEQ ID NO: 12:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 12:

AATCCGTCGA GCAGAGTTAG CCCGGTTAGG GTTAGGGTTA GCCGCGC                                    47
```

TELOMERASE ACTIVITY ASSAYS

CROSS-REFERENCE TO RELATED APPLICATIONS

This application is a continuation-in-part of copending Ser. No. 08/255,774, filed 7 Jun. 1994; which is a continuation-in-part of copending application Ser. No. 08/151,477, filed 12 Nov. 1993; and which is a continuation-in-part of copending application Ser. No. 08/153,051, filed 12 Nov. 1993.

FIELD OF THE INVENTION

The present invention relates to telomerase, a ribonucleoprotein enzyme involved in telomere DNA synthesis, and provides assays and protocols for identifying and measuring telomerase activity. The invention provides methods and compositions relating to the fields of molecular biology, chemistry, pharmacology, and medical diagnostic and prognostic technology.

DESCRIPTION OF RELATED DISCLOSURES

Telomeres are specialized structures at the ends of eukaryotic chromosomes and appear to function in chromosome stabilization, positioning, and replication (Blackburn and Szostak, 1984, *Ann. Rev. Biochem.* 53:163–194; Zakian, 1989, *Ann. Rev. Genetics* 23:579–604; Blackburn, 1991 *Nature* 350:569–573). In all vertebrates, telomeres consist of hundreds to thousands of tandem repeats of 5'-TTAGGG-3' sequence and associated proteins (Blackburn, 1991; Moyzis et al., 1988, *Proc. Natl. Acad. Sci.* 85:6622–6626). Southern blot analysis of chromosome terminal restriction fragments (TRF) provides the composite lengths of all telomeres in a cell population (Harley et al., 1990, *Nature* 345:458–460; Allsopp et al., 1992, *Proc. Natl. Acad. Sci. USA* 89:10114–10118; Vaziri et al., 1993, *Am. J. Human Genetics* 52:661–667). In all normal somatic cells examined to date, TRF analysis has shown that the chromosomes lose about 50–200 nucleotides of telomeric sequence per cell division, consistent with the inability of DNA polymerase to replicate linear DNA to the ends (Harley et al., 1990; Allsopp et al., 1992; Vaziri et al., 1993; Watson, 1972, *Nature New Biology* 239:197–201).

This shortening of telomeres has been proposed to be the mitotic clock by which cells count their divisions (Harley, 1991, *Mut. Res.* 256:271–282), and a sufficiently short telomere(s) may be the signal for replicatire senescence in normal cells (Allsopp et al., 1992; Vaziri et al., 1993; Hastie et al., 1990, *Nature* 346:866–868; Lindsey et al., 1991, *Mut. Res.* 256:45–8; Wright and Shay, 1992, *Trends Genetics* 8:193–197). In contrast, the vast majority of immortal cells examined to date show no net loss of telomere length or sequence with cell divisions, suggesting that maintenance of telomeres is required for cells to escape from replicatire senescence and proliferate indefinitely (Counter et al., 1992, *EMBO* 11:1921–1929; Counter et al., 1994, *Proc. Natl. Acad. Sci. USA* 91:2900–2940).

Telomerase, a unique ribonucleoprotein DNA polymerase, is the only enzyme known to synthesize telomeric DNA at chromosomal ends using as a template a sequence contained within the RNA component of the enzyme (Greider and Blackburn, 1985, *Cell* 43:405–413; Greider and Blackburn, 1989, *Nature* 337:331–337; Yu et al., 1990, *Nature* 344:126–132; Blackburn, 1992, *Ann. Rev. Biochem.* 61:113–129). With regard to human cells and tissues, telomerase activity has been identified in immortal cell lines and in ovarian carcinoma but has not been detected in mortal cell strains or in normal non-germline tissues (Counter et al., 1992; Counter et al., 1994; Morin, 1989, *Cell* 59:521–529). Together with TRF analysis, these results suggest telomerase activity is directly involved in telomere maintenance, linking this enzyme to cell immortality.

Methods for detecting telomerase activity, as well as for identifying compounds that regulate or affect telomerase activity, together with methods for therapy or diagnosis of cellular senescence and immortalization by controlling or measuring telomere length and telomerase activity, have also been described. See PCT patent publication No. 93/23572, published Nov. 25, 1993, incorporated herein by reference. The identification of compounds affecting telomerase activity provides important benefits to efforts at treating human disease. Compounds that inhibit telomerase activity can be used to treat cancer, as cancer cells express and require telomerase activity for immortality, and normal human somatic cells do not express telomerase activity at detectable levels. Compounds that stimulate or activate telomerase activity can be used to treat age-related diseases and other conditions relating to cell senescence.

While new and improved methods for screening to identify compounds that modulate telomerase activity have been developed. There remains a need for sensitive, reliable assays for detecting and measuring telomerase activity. Current methods for assaying telomerase activity in cell samples rely on the incorporation of radioactively labeled nucleotides into a telomerase substrate (Morin, 1989 supra). The conventional assay uses an oligonucleotide substrate, a radioactive deoxyribonucleoside triphosphate (dNTP) for labeling, and gel electrophoresis for resolution and display of products. Because telomerase stalls and can release the DNA after adding the first G in the 5'-TTAGGG-3' telomeric repeat, the characteristic pattern of products on the gel is a six nucleotide ladder of extended oligonucleotide substrates. The phase of the repeats depends on the 3'-end sequence of the substrate; telomerase recognizes where the end is in the repeat and synthesizes accordingly to yield contiguous repeat sequences. Although telomeric sequence oligonucleotides are efficient in vitro substrates, telomerase will also synthesize repeats using substrates comprising non-telomeric DNA sequences.

Using such methods, scientists have found that reliable telomerase extraction by hypotonic swelling and physical disruption of cells requires at least $10^4$–$10^8$ cells and that the extraction efficiency varies between cell types (Counter et al., 1992; Morin, 1989). There remains a need for telomerase activity assays with increased sensitivity, speed, and efficiency of detecting telomerase activity as compared to the conventional assay, and this invention meets that need.

SUMMARY OF THE INVENTION

The present invention provides a method for determining whether a cell sample contains telomerase activity and related reagents and materials useful for practice of the method. The method comprises the steps of:

(a) preparing a cell extract from said cell sample;

(b) placing an aliquot of said cell extract in a reaction mixture comprising a telomerase substrate lacking a telomeric repeat sequence and a buffer in which telomerase can catalyze extension of said telomerase substrate by addition of telomeric repeat sequences;

(c) adding to said reaction mixture a primer comprising a sequence sufficiently complementary to a telomeric repeat to hybridize specifically thereto under conditions such that if an extended telomerase substrate is present in said reaction mixture, said primer will hybridize to said extended telomerase substrate and extend to form a complementary copy of said extended telomerase substrate; and (d) correlating presence of telomerase activity in said cell sample with presence of duplex DNA molecules comprising an extended telomerase substrate bound to an extended primer and absence of telomerase activity in said cell sample with absence of said duplex DNA molecules.

The present invention also provides reagents and related methods useful in the practice of the invention. One such related method involves the extraction of telomerase activity from a cell sample. According to a method of the present invention, the extraction is conducted in a buffer that comprises a non-ionic and/or a zwitterionic detergent.

The telomerase activity extracted is used to mediate extension of a telomerase substrate in a telomerase substrate extension reaction. Another important step of the telomerase activity assay of the present invention also involves extension of an oligonucleotide "primer", and a number of useful reagents of the invention relate to this step. Typically, primer extension is mediated using a template-dependent DNA polymerase, and the primer is extended by addition of nucleotides to the primer by the DNA polymerase.

The DNA polymerase is preferably a thermostable DNA polymerase; using such a polymerase, one can conduct multiple cycles of primer extension, each cycle comprising the steps of (1) heating the reaction mixture to denature duplex DNA molecules; and (2) cooling the reaction mixture to a temperature at which complementary nucleic acids can hybridize and the polymerase can extend the primer, without inactivating the polymerase. In this embodiment of the method, one can also take advantage of the powerful Polymerase Chain Reaction ("PCR") technology by having an excess amount of the telomerase substrate, which serves as the second primer for the PCR, in the reaction mixture and performing the heating and cooling steps 5, 10, 15, 20, 30, or more times.

Alternatively, the primer extension can be mediated by a template-dependent DNA ligase, so that the primer is extended by addition of an oligodeoxyribonucleotide to the primer by the DNA ligase. Typically, the DNA ligase is a thermostable DNA ligase, and the primer extension step is conducted by (1) heating the reaction mixture to denature duplex DNA molecules; and (2) cooling the reaction mixture to a temperature at which complementary nucleic acids can hybridize and the ligase can extend the primer. In this embodiment of the method, one can also take advantage of the powerful Ligase Chain Reaction ("LCR") technology by having oligonucleotides ("ligomers") complementary to the extended primer in the reaction mixture and by performing the heating and cooling steps from 5, 10, 15, 20, 30, or more times.

The present invention also provides a number of oligonucleotides, such as primers and oligomers, useful in the practice of the present invention. For instance, when one is using PCR to amplify a nucleic acid, one needs to avoid non-specific product formation. Such products can form by a variety of methods, including via interaction of the primers used in the process to form "primer-dimer." The present invention provides primers designed specifically to minimize the problem of primer-dimer formation. In another aspect, the invention provides primers that comprise a non-telomeric repeat sequence (a sequence neither identical nor complementary to a telomeric repeat sequence) at the 5'-end of the primer. The use of such primers, called "anchored primers", in the present invention provides a means by which one can assure that the largest primer extension product has no more telomeric repeats than do the largest products of telomerase-mediated extension of the telomerase substrate. Without such primers, multiple cycles of primer extension and product denaturation can yield primer extension products that comprise many more telomeric repeats than present in the telomerase-extended telomerase substrates in the reaction mixture.

The present invention also provides novel configurations of the reagents useful in the telomerase activity assay and kits comprising those reagents to facilitate practice of the method. The activity assay is typically conducted in a single reaction tube, which provides a convenient format for packaging the reaction components. For instance, one can prepare the reagents so that the primer is sealed under a wax layer or barrier at the bottom of the tube, and the telomerase substrate and optionally the buffer and polymerase (or ligase) are positioned on top of the barrier. When the tube is heated at the conclusion of the telomerase-mediated telomerase substrate extension step, the wax barrier melts, allowing the primer to mix with the other reaction components. This format ensures that the primer will be accessible to the DNA polymerase and any extended telomerase substrates only at temperatures that ensure highly specific nucleic acid base-pairing and so reduces non-specific primer extension and primer-dimer (composed of a primer and an unextended telomerase substrate) formation. Thus, one useful kit of the invention comprises a reaction tube containing a primer sealed beneath a wax barrier over which the telomerase reaction buffer (optionally comprising a thermostable polymerase or ligase) sits.

The various reagents can also be labelled to facilitate identification of telomerase-extended telomerase substrate. Thus, one can use a labelled nucleoside triphosphate and monitor incorporation of the labelled nucleotides in the telomerase substrate or primer. For more accurate quantification of telomerase activity, however, one can use a labelled telomerase substrate or primer. Any of a wide variety of labels can be used for purposes of the present invention. Such labels typically include fluorescent, phosphorescent, chemiluminescent, and radioactive labels. Alternatively, the label can merely be an unlabelled "tag", which in turn is recognized by a labelled molecule that binds to the tag. For instance, one can use biotin as the tag, use avidinylated horseradish peroxidase ("HRP") to bind to the tag, and then use a chromogenic substrate (i.e., TMB) to detect the presence of the HRP. In similar fashion, the tag can be an epitope or antigen, and a fluorescently or radioactively labelled antibody can be used to bind to the tag.

The present invention also provides means other than (or in addition to) a label to provide a quantitative assay for telomerase activity. In this aspect of the invention, a control oligonucleotide consisting essentially of (in the 5'-to-3' direction) the telomerase substrate, a "stuffer" sequence of known length (preferably 3 bases) and composition, a specific number of telomeric repeat sequences, and a sequence complementary to the primer used in the primer extension step (which primer might optionally comprise an anchor sequence) is added in known amounts to the reaction mixture at the beginning of the reaction. Use of this internal control not only facilitates the determination of whether the assay was conducted properly but also facilitates quantification of the telomerase activity present in the sample. The control oligonucleotide can also be conveniently packaged into a kit with other reaction components.

While the methods of the invention are broadly applicable to the detection of telomerase activity in any sample from any origin, the methods are especially useful and applicable to the detection of telomerase activity in samples of biological material obtained from humans. Such samples will contain cells or cellular materials and will typically be obtained from humans for purposes of detecting cancer. Telomerase is not expressed by normal post-natal human somatic cells, although low levels of telomerase activity can be detected in certain stem cells and activated cells of the hematopoietic system, so the presence of telomerase activity in a sample of human somatic tissue or cells indicates that immortal cells, including certain types of cancer cells, are present in the tissue. While not all cancer cells express telomerase activity, telomerase expression is required for cells to become immortal. Consequently, the presence of cells with telomerase activity is associated with many forms of cancer and can also serve to indicate that a particularly invasive or metastatic form of cancer is present.

Thus, the invention provides a method for diagnosis of a condition in a patient associated with an elevated level of telomerase activity within a cell. The method involves determining the presence or amount of telomerase activity within the cells of the patient, and the method is therefore applicable to the detection of elevated levels of telomerase activity associated with prostate cancer, breast cancer, colon cancer, renal cancer, ovarian/cervical cancer, lung cancer, and leukemia. The method involves determining the presence or amount of telomerase activity within the cells by telomerase substrate and primer extension reactions, preferably employing the polymerase chain reaction.

These and other aspects of the invention are described in more detail below, beginning with a brief description of the accompanying drawings.

BRIEF DESCRIPTION OF THE DRAWINGS

In FIG. 1, part A, CHAPS-extracted cell preparations are used in the conventional assay, and the results show the extracts perform as expected. See Example 1, below. In FIG. 1, part B, the telomerase substrate "TS" (SEQ ID NO:1) is shown together with a TS telomerase extension product (with about 4 telomeric repeat sequences; the number of repeat sequences can vary from extension product to extension product), which is shown duplexed (vertical lines indicate base-pairing and asterisks indicate mismatches, which were incorporated into the design of the primer to minimize interaction of the primer with unextended telomerase substrate) with the "CX" primer (SEQ ID NO:2). Broken arrows in this Figure represent the potential primer extension products formed during the PCR step; the potential extension product of the CX primer is shown sandwiched between actual and potential TS extension products. FIG. 1, part D, shows the results of multiple control experiments demonstrating that a positive signal in the present method (which is also referred to as the "Telomerase Repeat Amplification Protocol" or "TRAP") requires a ribonucleoprotein in an immortal cell extract capable of extending the TS oligonucleotide with three or more 5'-TTAGGG-3' repeats, validating the assay for specific detection of telomerase activity (see Example 2, below). FIG. 1, part E, shows the results of analyzing a variety of samples containing differing levels of telomerase activity to illustrate the increased sensitivity of the present method (see Example 2, below)

DESCRIPTION OF THE PREFERRED EMBODIMENTS

The present invention provides novel methods and reagents for the extraction and detection of telomerase activity. Together, these improvements result in an estimated $10^4$ fold improvement over the conventional method for detection of telomerase activity. Telomerase synthesizes telomeric DNA at the ends of chromosomes and is believed to be necessary for indefinite proliferation of immortal cells. Analysis of chromosome terminal restriction fragments in a wide variety of human cell types has shown that telomere length and sequence are stably maintained in immortal cell lines but not in dividing cultures of normal somatic cells. The association of telomerase with immortality has been difficult to establish due to the limited sensitivity of the conventional activity assay, which relies on the incorporation of radioactively-labelled nucleotides into a telomerase substrate to form a labelled telomerase substrate extension product.

The methods of the present invention have been used to test for telomerase activity in human cell lines and normal somatic cells representing 18 different tissues of origin. Extracts from 68 of 68 tumor-derived cell lines, 4 of 6 transformed cell lines, and none of 22 normal somatic cell cultures tested positive for telomerase activity (Example 3 below). The difference in telomerase activity between immortal and normal somatic cells was estimated to be at least 1000 fold. These findings support the direct role for telomerase in telomere dynamics in human cells.

In addition to providing an improved telomerase activity assay, the present invention provides a novel detergent lysis method that provides more uniform extraction of telomerase activity even at low cell numbers. The method involves the steps of: (1) collecting a sample of cells; (2) lysing said sample in a lysis buffer comprising 0.01 to 5% of a non-ionic and/or a zwitterionic detergent; (3) removing cellular debris by centrifugation; and (4) collecting supernatant separated from said cellular debris. A wide variety of non-ionic and/or zwitterionic detergents can be employed in the method. Preferred non-ionic detergents include TWEEN 20, TRITON X-100, TRITON X-114, THESIT, NP-40, n-octylglucoside, n-dodecylglucoside, n-dodecyl-beta-D-maltoside, octanoyl-N-methylglucamide (MEGA-8), decanoyl-N-methylglucamide (MEGA-10), and isotridecyl-poly(ethyleneglycolether)$_n$, and preferred zwitterionic detergents include CHAPS (3-{(3-cholamidopropyl) dimethylammonio}-1-propane-sulfonate), CHAPSO (3-{(3-cholamidopropyl)dimethyl-ammonio}-2-hydroxy-1-propane-sulfonate), N-dodecyl-N,N-dimethyl-3-ammonio-1-propane-sulfonate, and digitonin, with CHAPS a particularly preferred detergent. While the exact amount of detergent is not critical, 0.5% is typically sufficient to observe the enhanced extraction of telomerase activity.

Figure 1D:
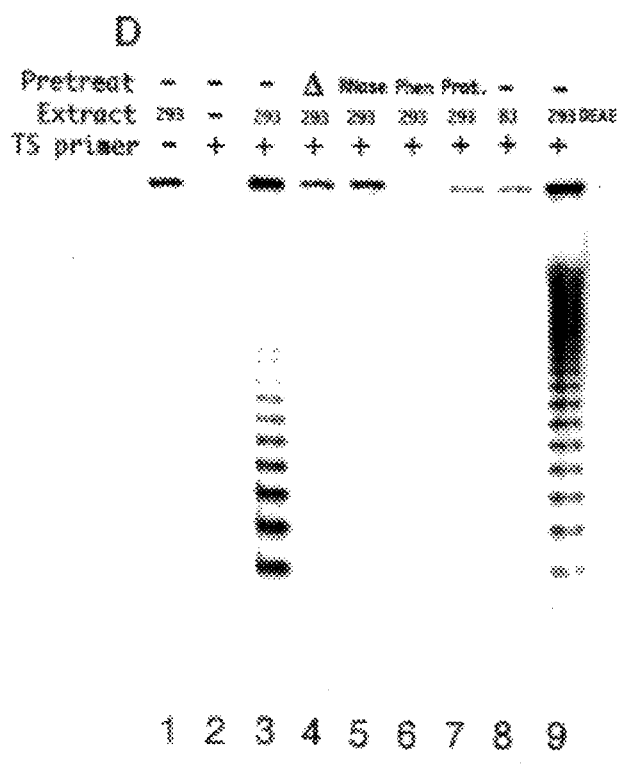
FIG. 1, in parts A, B, C, D, and E, shows the improved results obtained using the telomerase extraction method and activity assay of the present invention as compared with the conventional methodology.

Example 1, below, demonstrates that CHAPS-extracted telomerase activity functions as expected in the conventional telomerase activity assay. As shown in FIG. 1A, the detergent-extracted activity produces the six nucleotide ladder of extension products (lanes 1, 2, and 4) characteristic of telomerase activity; there is a shift in product phase dependent upon the 3'-sequence of the oligonucleotide telomerase substrate (compare lanes 1, 2, and 4), as is expected for telomerase-mediated extension; that the activity extracted can extend a non-telomeric oligonucleotide previously shown to be a telomerase substrate (Morin, 1991, *Nature* 353:454–456; lanes 4 and 5) with 5'-TTAGGG-3' repeats (as confirmed using dideoxynucleotide chain termination sequencing); and that the activity was abolished by RNase treatment, as would be expected for telomerase activity (lanes 3 and 5; Greider and Blackburn, 1985, *Cell* 43:405–413; Greider and Blackburn, 1989, *Nature* 337:331–337; Morin, 1989, *Cell* 59:521–529).

While the telomerase activity assay of the present invention is not limited to the assay of cell samples from which extracts have been obtained using the detergent lysis method of the invention, such extracts are preferred, especially when only a few cells are available or the number of cells expressing telomerase activity in a sample is very low. The telomerase activity assay of the invention is far superior to the conventional assay in detecting telomerase activity in such circumstances, as well as being faster to complete and more efficient. This novel method involves the basic steps of:

(a) preparing a cell extract from said cell sample;

(b) placing an aliquot of said cell extract in a reaction mixture comprising a telomerase substrate lacking a telomeric repeat sequence and a buffer in which telomerase can catalyze extension of said telomerase substrate by addition of telomeric repeat sequences;

(c) adding to said reaction mixture a primer comprising a sequence sufficiently complementary to a telomeric repeat to hybridize specifically thereto under conditions such that if an extended telomerase substrate is present in said reaction mixture, said primer will hybridize to said extended telomerase substrate and extend to form a complementary copy of said extended telomerase substrate; and (d) correlating presence of telomerase activity in said cell sample with presence of duplex DNA molecules comprising an extended telomerase substrate bound to an extended primer and absence of telomerase activity in said cell sample with absence of said duplex DNA molecules.

The method of the invention essentially involves two key reactions: (1) telomerase-mediated extension of a telomerase substrate; and (2) a primer extension reaction that proceeds only if telomerase-extended substrates have been produced by telomerase activity present in the sample. For a more complete understanding of the invention, one should first consider some global issues relating to (1) the nature of the sample; (2) the important features of the telomerase substrate; and (3) the nature of the primer extension reaction and the primers and extension reagents used in that reaction.

Any type of sample can be tested by the method. Samples of particular interest include cell samples, which can be tissue or tumor samples, obtained for purposes of diagnostic analysis. The expression of telomerase activity in a variety of cells has been studied and discussed in the scientific literature. Telomerase is expressed not only by eukaryotic cell pathogens but also by immortal human cells, including certain types of tumor and cancer cells, but is not expressed by cells of normal somatic (as opposed to germline) tissue, although low levels of telomerase activity can be detected in stem cells and in certain activated cells of the hematopoietic system. Consequently, samples might be obtained for the purpose of determining whether a telomerase-expressing pathogen or cancer or tumor cell is present. For such purposes, the sample will often be obtained from a human, but one can also readily understand that samples tested by the present method can be obtained from agriculturally important mammals, such as cattle, horses, sheep, etc., other animals of veterinary interest, such as cats and dogs, and from the environment, for environmental testing for the presence of pathogens.

Regardless of the origin of the sample, to practice the present method, one first prepares a cell extract, preferably using the detergent-based extraction method of the present invention, and then places that cell extract, or an aliquot of the cell extract, in a reaction mixture comprising a telomerase substrate and a buffer compatible with telomerase activity. The particular telomerase substrate chosen may vary depending on the type or origin of the telomerase activity for which one is testing. The telomerase activity expressed by one organism may differ with respect to substrate specificity from that expressed by another organism. Consequently, if one is using the method to determine whether a cancer cell of human origin is present in the sample, one employs a telomerase substrate recognized by human telomerase.

A variety of substrates are known for the telomerases of Tetrahymena and human cells and can readily be identified for other types of cells. However, when one employs a DNA polymerase-based primer extension step, the present method requires that the telomerase substrate not comprise a telomeric repeat sequence. Those of skill in the art will recognize that the telomeric repeat sequence produced by telomerase activity will depend upon the origin of the telomerase. For instance, Tetrahymena telomerase adds repeats of sequence 5'-TTGGGG-3' to the ends of telomerase substrates, while human telomerase adds repeats of sequence 5'-TTAGGG-3' Thus, if one is using the present method to assay for human telomerase activity, the telomerase substrate should be a human telomerase substrate lacking the sequence 5'-TTAGGG-3'. There is no requirement that a human telomerase substrate lack a telomeric repeat sequence from an organism that has a telomerase that adds a different repeat, so long as the presence of that different repeat sequence does not produce undesired results, such as excessive primer-dimer formation, as discussed below.

This requirement for the telomerase substrate to lack telomeric repeat sequences arises out of the second reaction of the present method—the non-telomerase-mediated primer extension reaction. In this reaction, an oligonucleotide primer that hybridizes only to extended telomerase substrates is added to the reaction mixture under conditions such that, if extended telomerase substrates are present, the primer binds to the extended substrates and is then extended by enzymatic action. Because telomerase can extend the telomerase substrate only by the addition of telomeric repeats, the primer will necessarily comprise a sequence complementary to a telomeric repeat. If the telomerase substrate employed in the telomerase extension reaction comprised a telomeric repeat, then the primer employed in the primer extension reaction could hybridize to unextended telomerase substrate, with potentially negative consequences. The telomerase substrate can, however, comprise sequences highly related to a telomeric repeat sequence without compromising the validity of the results obtained. For instance, an especially preferred human telomerase substrate of the invention is oligonucleotide M2, also known as TS (SEQ ID. NO.1), which contains a sequence at its 3'-end that is identical to five of the six bases of the human telomeric repeat but otherwise contains no telomeric repeat sequences.

The primer extension reaction serves to amplify the signal produced by the presence of telomerase activity in a sample (extended telomerase substrates) by producing a second signal, extended primers. The primers can be extended by any means that requires the presence of extended telomerase substrates for primer extension to occur; two preferred means are mediated either by a template-dependent DNA polymerase or a template-dependent DNA ligase. With either of these means, if telomerase activity is present in the sample, an extended telomerase substrate is formed and then hybridizes to a primer, providing a substrate for either DNA polymerase or DNA ligase to produce a primer extension product.

Once a primer extension product has formed, one can disassociate (typically by heating, but one could also use an enzyme or chemical process, such as treatment with helicase) the extended primer from the extended substrate. If additional primer and primer extension reagent is present in the sample, then a new primer/extended telomerase substrate complex can form, leading to the production of another extended primer. One can repeat the process of primer extension and denaturation several to many times, depending upon the amount of signal desired. Typically, primer extension and denaturation of extended primer/extended telomerase substrate complexes will be performed at least 5, 10, 15, 20 to 30 or more times. Moreover, if a second primer complementary to the 3'-end of the extended primer is present in the reaction mixture, one can increase the signal (both extended primer and also additional extended telomerase substrate) dramatically. Unextended telomerase substrate still present in the reaction mixture during the primer extension step could function as such a second primer.

Those of skill in the art will recognize that if the primer extension reagent is a DNA polymerase and a second primer is present, one has the requisite components for a polymerase chain reaction, more fully described in U.S. Pat. Nos. 4,683,195 and 4,683,202, provided the appropriate buffer and nucleoside triphosphates are present in the reaction mixture. PCR amplification is the preferred mode for conducting the primer extension reaction step of the present invention and dramatically increases sensitivity, speed, and efficiency of detecting telomerase activity as compared to the conventional assay. The protocol is termed "TRAP" for Telomeric Repeat Amplification Protocol and is illustrated in Example 2 and FIG. 1, parts B–E). In this embodiment of the invention, the telomerase substrate also serves as a PCR primer (termed the "upstream primer"). The sequence of the other primer is chosen to avoid annealing of the telomerase substrate and the primer, because even minor levels of primer/telomerase substrate annealing can yield early cycle PCR products identical to telomerase products (i.e., TS (SEQ ID. NO:1) plus (5'-TTAGGGG-3')$_n$). In subsequent cycles, these products would serve as template for the production of PCR products, potentially resulting in a false positive.

The present invention provides a variety of oligonucleotide primers and telomerase substrates for use in the PCR-based embodiment of the present invention. One such primer (termed the "downstream primer") is designated "CX" and is composed of sequences complementary to three imperfect telomeric repeats and one perfect repeat (5'-(CCCTTA)$_3$CCCTAA-3') (SEQ ID NO.2). The single nucleotide difference in three of the repeats compromises the capacity of CX (SEQ ID NO.2) to anneal to the telomerase substrate TS (SEQ ID NO.1) (which, as noted above, contains 5 of 6 nucleotides of a telomeric repeat), thereby minimizing the formation of non-specific PCR products, such as primer-dimer. Any possible alignment between these primers (CX (SEQ ID NO.2) and TS (SEQ ID NO.1) nucleated by the telomeric sequence complementarity leads to a duplex in which the recessed 3' nucleotide is mismatched and so is not efficiently extended by polymerase.

As the CX primer (SEQ ID NO.2) demonstrates, and as those of skill in the art will recognize upon review of this disclosure, a primer with sequences "complementary to a telomeric repeat" includes a primer that may contain one or more mismatched bases with respect to the telomerase substrate extension product to which the primer is intended to hybridize. The number of mismatches that can be tolerated within this definition can vary depending upon the length and sequence composition of the primer, the temperature and reaction conditions employed during the PCR step, the purpose for which the assay is conducted, and the results desired.

In addition to primer CX (SEQ ID NO.2), the present invention provides several modifications of a basic PCR that, while not necessary to obtain the benefits of the present method, greatly enhance the specificity, sensitivity, and efficiency of the present method. For instance, one important modification relates to the buffer: the present invention provides a buffer in which both telomerase activity and DNA polymerase activity can be observed. The use of such a buffer allows the artisan to conduct both the telomerase substrate extension reaction and the primer extension reaction in the same reaction vessel (typically a tube: see Example 2 and FIG. 1, part C).

Another modification relates to the use of short oligonucleotides that are complementary to either the telomerase substrate or the primer in the reaction mixture. These short oligonucleotides are designed to have a melting temperature (with respect to the primer or telomerase substrate to which the short oligonucleotides hybridize) about 10° C. lower than the annealing temperature of the primers used in the primer extension step and to prevent primer-dimer formation and/or non-specific primer extension. The short oligonucleotides melt away from their complementary oligonucleotides at temperatures just below the ideal annealing temperatures for the primer extension step, preventing inappropriate primer extension at lower, non-specific temperatures. If the short oligonucleotide is designed to hybridize to the telomerase substrate, sufficient single-stranded region (about 3 bases) must remain at the 3'-end of the telomerase substrate when hybridized to the short oligonucleotide to allow telomerase-mediated extension to occur. Given that the short oligonucleotides are not intended to serve as primers for DNA synthesis, the 3'-end of the short oligonucleotide can be blocked to prevent addition of nucleotides to the short oligonucleotide. If the short oligonucleotide is designed to hybridize to the primer, then the 3'-end of the short oligonucleotide should be blocked (i.e., with biotin or an amino group) to prevent the short oligonucleotide from serving as a telomerase substrate.

A variety of other reagents and formats can be employed, as illustrated in Example 2, to ensure a high degree of specificity, including: (1) separation of the primer from the other reaction components by a wax barrier that melts only after the reaction mixture is heated at the end of the telomerase-mediated extension reaction; (2) the use of T4 gene 32 protein (Clontech); and (3) the use of TAQSTART™ antibody. Those of skill in the art will recognize that the reagents employed to generate the results described in Example 2 are commercially available or, in the case of the oligonucleotides, can be prepared using commercially available instrumentation and that a wide variety of DNA polymerases, antibodies, and single-strand DNA binding proteins can be employed in the method.

Figure 1E:
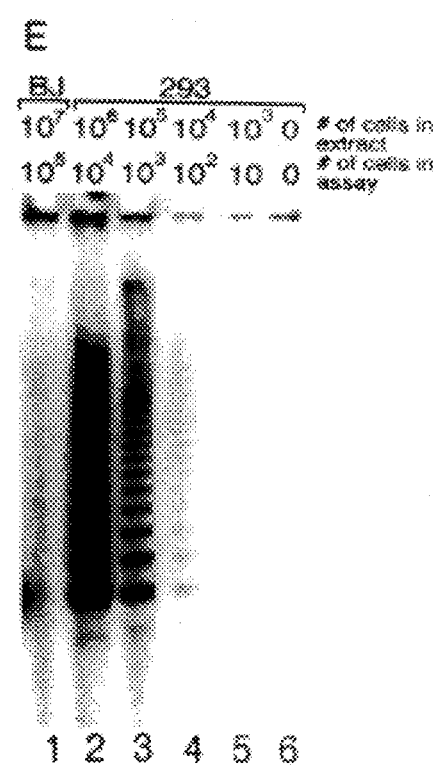

As shown by the results reported in Example 2 and in FIG. 1, part E, telomerase-positive extracts from human 293 kidney cells were produced routinely from $10^5$ cells, as assessed by TRAP assay (FIG. 1, part E, lane 3), with a lower limit for the conditions employed in the Example of $10^4$ cells for CHAPS extraction (lane 4). A quantity of extract representing $10^3$ cells (1% of an extract from $10^5$ cells) reproducibly gave a clear positive signal in the TRAP assay (FIG. 1, part E, lane 3) with a lower limit for the conditions employed in the Example of $10^2$ cell equivalents for detection of telomerase activity (lane 4). These results demonstrate at least 100 fold improvements in both extraction efficiency and telomerase activity detection when compared to conventional methods and together increase current detectability of telomerase activity by a factor of $10^4$. Detection in $10^2$ immortal cells (FIG. 1, part E, lane 4) and not in $10^5$ BJ cells (lane 1) indicates that the difference in telomerase activity between immortal and normal somatic cells is at least three orders of magnitude.

Those of skill in the art will recognize the detection limits noted above are valid only if one employs merely routine procedures and that the present method can be used to detect telomerase activity in a single cell, provided one is willing to use effort somewhat greater than what is typically considered routine. For instance, one could increase the time of the telomerase-mediated extension step and increase the number of primer extension cycles to increase the sensitivity of the assay to detect telomerase activity in a few cells or a single cell.

Figure 2A:
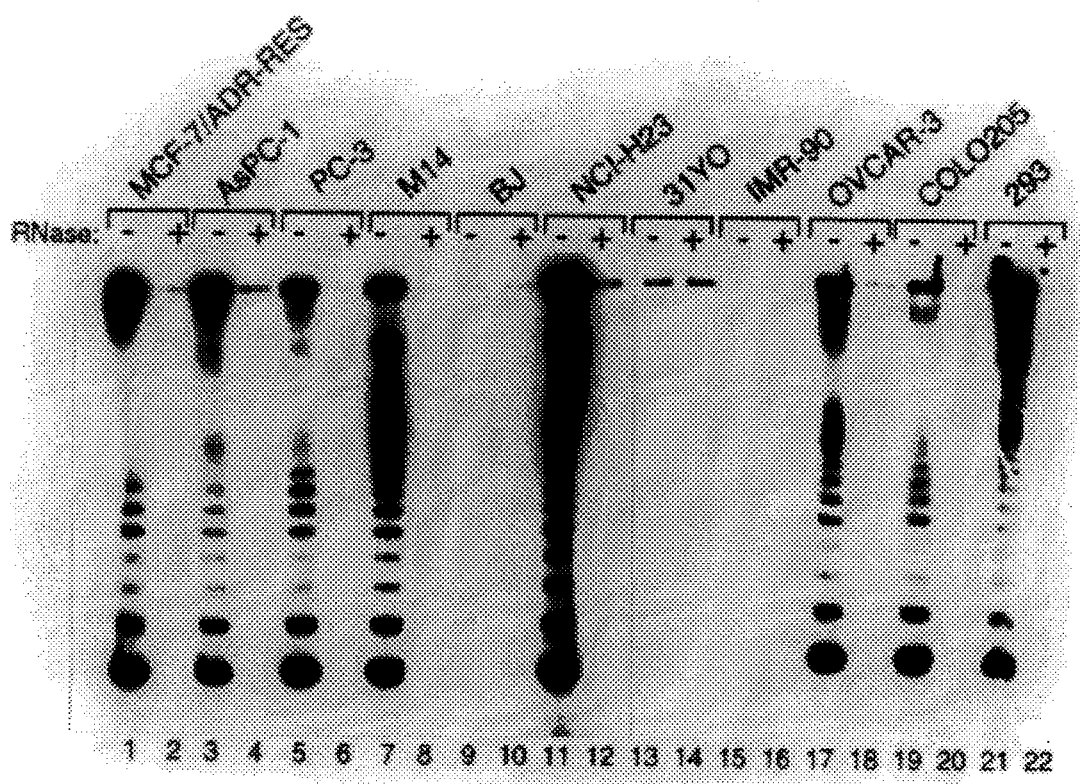
FIG. 2 shows a comparison of the present method (FIG. 2, part A) and a conventional assay (FIG. 2, part B) performed on the same 10 cell extracts, which were prepared from immortal cell lines and normal somatic cell cultures using the CHAPS detergent lysis method (see Examples 1 and 3, below).
Figure 2B:
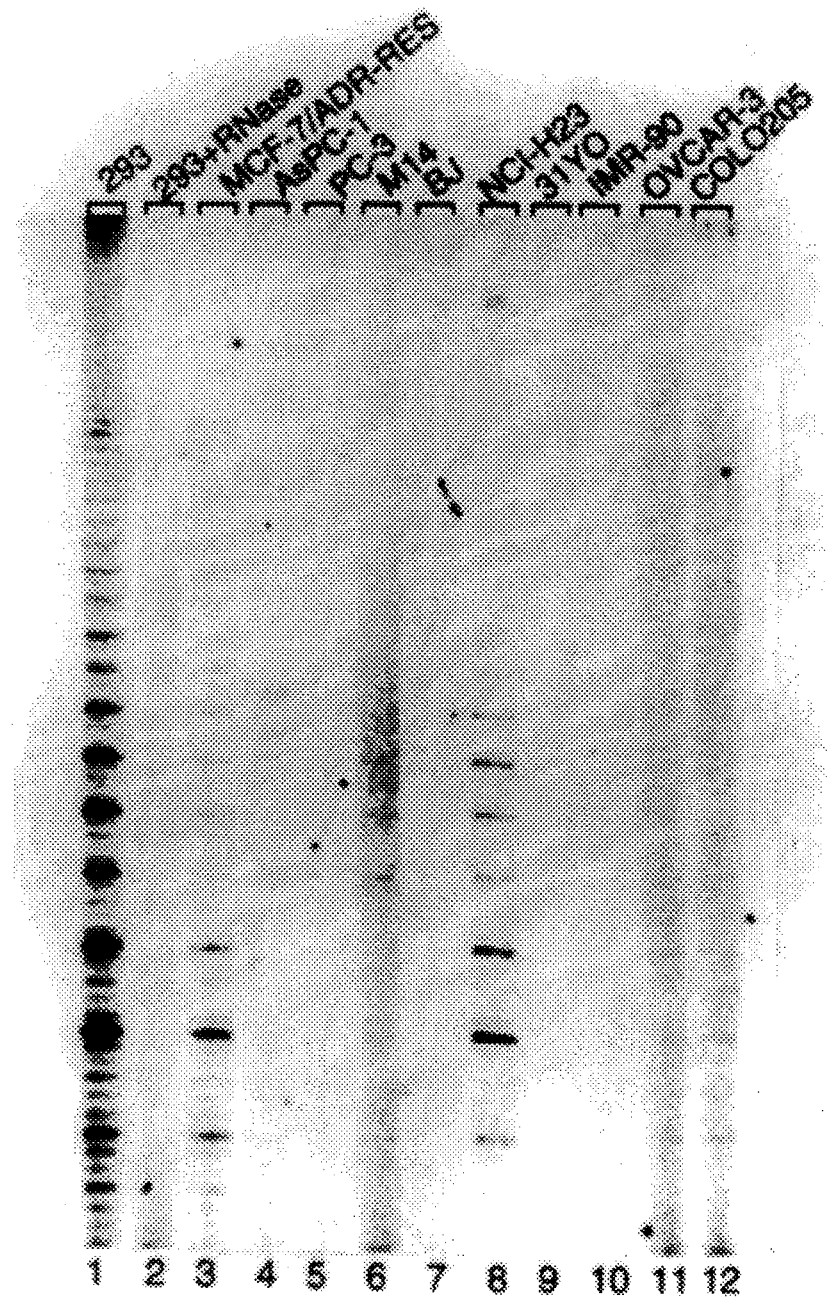

The telomerase activity assay method of Example 2 has been used to test for telomerase activity in various immortal cell lines and normal somatic cell cultures from different tissues and individuals. FIG. 2 shows a comparison of TRAP assays (FIG. 2, part A) and conventional assays (FIG. 2, part B) performed on the same 10 cell extracts, which were prepared using the CHAPS detergent lysis method (see Examples 1 and 3, below). Some cell lines (293, MCF-7/ADR-RES, NCI-H23, OVCAR-3, COLO205, M14) show activity in both assays, others (AsPC-1 and PC-3) show activity only in the TRAP assay, and the normal somatic cell cultures (BJ, IMR-90 and 31YO) show no detectable activity by either assay. These results demonstrate that the TRAP method can detect telomerase activity in extracts that test negative by the conventional assay.

This survey was expanded to include a total of 74 immortal cell lines and 22 normal somatic cell cultures from 18 different tissues, and the results are summarized in Table 1 (see Example 3, below). None of the normal somatic cell cultures displayed detectable telomerase activity in the TRAP assay. Of the 74 immortal cell lines, 68 were tumor-derived lines and 6 were cell lines transformed with viral oncoproteins. All of the 68 tumor lines contained telomerase activity. Two of the six transformed lines tested negative for telomerase activity. If these two lines are immortal, then the lack of detectable telomerase activity is unexpected. However, an investigation of telomere length in these lines showed that the telomeres were longer than those of the normal somatic cells from which the lines were derived, which may indicate that the cells experienced a transient burst of telomerase activity. If the telomerase activity is not reinitiated, then the cells may not possess unlimited replicative capacity.

As the results described above and in Examples 1 to 3, below, demonstrate, the PCR-based embodiment of the present invention offers significant improvements over currently available methods for measuring telomerase activity in a sample. Other novel variations of the present method, however, also offer significant advantages. In particular, the present method can be used to quantitate the telomerase activity in a sample by providing the number of telomerase products generated per unit time. To understand the nature of these improvements, however, one first might consider more carefully the results obtained using the assay described in Example 2, as depicted in FIGS. 1 and 2. As one can note from those Figures, the ladder of bands produced upon gel electrophoresis of the assayed samples extends up the gel. Such results might reflect the number of repeats added by telomerase during the telomerase-mediated extension reaction or could result from staggered binding of primers during PCR amplification.

The phrase "staggered binding" refers to the binding of a primer to a sequence in an extended telomerase substrate in a manner that leaves the 3'-end of the extended telomerase substrate recessed and therefore available for extension by DNA polymerase. DNA polymerase can then add nucleotides to the 3'-end of the extended telomerase substrate, creating molecules longer than those produced in the telomerase-mediated extension step. To determine whether staggered binding was occurring in reactions such as those described in Example 2, synthetic oligonucleotides representing discrete telomerase extension products, e.g., TS+4 (TS plus four telomeric repeats), were used to develop specific amplification conditions. Even under high stringency, staggered annealing of the downstream primer occurred (e.g., annealing by 3 of the 4 repeats). Hence PCR amplification of a discrete telomerase extension product yielded a six nucleotide ladder of PCR products increasing in size up to the limit of gel resolution. Thus, TRAP assay products produced using a primer such as CX (SEQ ID NO:2) are not directly reflective of the length distribution of telomerase products generated in the assay, due to the staggered binding of primers to templates during the primer extension reactions.

To prevent such interaction from generating products with more repeats than telomerase added to the substrate, one can employ a novel "anchored" primer of the invention as the downstream primer in the assay. The oligonucleotide ACT (SEQ ID NO:3) (see Example 4) is a 24 nucleotide oligonucleotide primer that comprises a 6 nucleotide anchor sequence at its 5'-end and three repeats of CTR (C-rich telomeric repeat) sequences (5'-CTAACC-3'). For purposes of the present invention, an anchor sequence is a 5'-terminal sequence of a PCR primer that is non-complementary and non-identical to a telomeric repeat sequence and that prevents the PCR product from "growing" on itself as observed when the primer pairs TS/CTR4 (SEQ ID NO.1/SEQ ID NO.11) or TS/CX (SEQ ID NO.1/SEQ ID NO.2) are employed.

A wide variety of anchor sequences can be employed. In one embodiment, the anchor sequence is the sequence of the telomerase substrate used in the telomerase-mediated extension step of the method, providing a "TS-anchored" primer. The anchored primer would thus comprise, in the 5'-to-3' direction, a telomerase substrate sequence and two or more complementary copies of the telomeric repeat sequence. By employing such a primer, one can practice the present method in what is essentially a "one primer" mode, because after the first round of primer extension, excess unextended telomerase substrate in the reaction mixture can prime the synthesis of both strands of the complex formed as a result of the first round of primer extension.

By using the primers TS (SEQ ID NO.1) and ACT (SEQ ID NO.3) (or another anchored primer) in the TRAP assay, one can deduce the Most Processive Product (MPP) of the telomerase in a given extract. The use of an anchored primer such as ACT (SEQ ID NO.3) prevents the growth of telomerase products into longer versions during PCR. With the ACT (SEQ ID NO.3) primer, the slowest migrating band reflects directly the length of the MPP of the original telomerase products before the PCR. The ACT (SEQ ID NO.3) primer is particularly preferred for purposes of the present invention in that it is more resistant to the types of primer-dimer interactions observed between TS (SEQ ID NO.1) and primers such as CX (SEQ ID NO.2) or CTR4.

While the PCR-based embodiment of the present method has been described in detail above and is exemplified in the Examples below, the present method can be practiced using any method of primer extension. While PCR provides for exponential accumulation of primer extension products, even linear accumulation of primer extension products can provide useful results. Thus, one can use a single primer and merely make many copies of a single strand of the duplex nucleic acid that is produced when PCR is employed.

Moreover, such copies can be made by means other than polymerase-mediated primer extension. Suitable methods include the ligase chain reaction (Barany, 1991, *Proc. Natl. Acad. Sci. USA* 88:189–193), nucleic acid sequence-based amplification (Compton, 1991, *Nature* 350:91–92), self-sustained sequence replication (Guatelli et al., 1990, *Proc. Natl. Acad. Sci. USA* 87:1874–1878), strand displacement amplification (Walker et al., 1992, *Proc. Natl. Acad. Sci. USA* 89:392–396), and branched DNA signal amplification (Urdea, 12 Sep. 1994, *Bio/Tech.* 12:926–928), although the latter method involves amplification of the signal produced upon probe hybridization to a target nucleic acid. As one example, DNA ligase can be used to ligate together two oligonucleotides hybridized to a template nucleic acid. If, as in PCR, the duplex nucleic acid is then denatured, then one can repeat the process of ligation and denaturation many times to accumulate many complementary copies of the original template, i.e., the extended telomerase substrate. If one additionally adds two other oligonucleotides complementary to the copy produced by ligation of the first two oligonucleotides on the extended telomerase substrate and selects those oligonucleotides such that DNA ligase can ligate the two together to form a copy of the original extended telomerase substrate, then one has the basic components of an LCR.

To illustrate, one could employ LCR in the present method using the following 4 oligonucleotide "ligomers":

LTS (5'-CCCAATCCGTCGAGCAGAGTTAG-3') (SEQ ID NO.4),

CLT (5'-TAACTCTGCTCGACGGATTCCC-3') (SEQ ID NO.5),

LC (5'-GGGTAACCCTAACCCTAACCC-3') (SEQ ID NO.6), and

LG (5'-GGTTAGGGTTAGGGTTAAA-3') (SEQ ID NO.7).

The LC and CLT ligomers will anneal to an extended telomerase substrate and then be ligated with DNA ligase to form a template for ligation of the LTS and LG ligomers. These ligomers have been selected so that no two ligomers can anneal to form a duplex nucleic acid that can be joined to another duplex nucleic acid in the mixture by the blunt-end ligation activity of DNA ligase. There is no requirement that the telomerase substrate be free of telomeric repeat sequences when the primer extension step of the present method is mediated by a ligase activity. A wide variety of such ligomers can be used in the method to minimize template-independent product formation. LCR amplification of telomerase extension products produces an amplified product of uniform size and so is conducive to quantitative analysis.

The present invention provides a variety of means to quantitate the amount of telomerase in a sample, although for most purposes, a qualitative result (telomerase activity present or absent) is sufficient. One important means for obtaining quantitative information is the use of a control oligonucleotide template added to each reaction mixture in a known amount, as illustrated below in Example 4.

An illustrative control oligonucleotide of the invention comprises, in 5'-to-3' order, a telomerase substrate sequence, a spacer sequence (optional: the presence of a spacer sequence, preferably 3 bases, but which can be any sequence of nucleotides or length, can alter spacing of the ladder produced by electrophoresis of reaction products produced from telomerase positive samples), a telomeric repeat sequence (typically present in multiple, i.e., 2 to 50, copies), and a sequence complementary to the primer used in the assay (and so which may simply be a portion of the telomeric repeat sequence and if the primer includes an anchor sequence, then optionally a sequence complementary to the anchor sequence). Of course, an oligonucleotide complementary to the control sequence defined above can also serve as the control sequence, and a double-stranded control nucleic acid can also be employed. Use of this internal control not only facilitates the determination of whether the assay was conducted properly but also facilitates quantitation of the telomerase activity present in the sample.

Alternatively, one can add a control nucleic acid of any sequence to the reaction mixture in known amounts and amplify the control with primers different from those used to amplify the extended telomerase substrate. The control oligonucleotide and/or the primers used to amplify the control oligonucleotide can be labelled identically to or differently from the label used to label the telomerase extension products. The control oligonucleotide can also be conveniently packaged into a kit with other reaction components.

Moreover, a variety of different types of oligonucleotides can be used as a control or in the steps of the method. While the discussion above and Examples below illustrate the invention with results obtained using deoxyribooligonucleotide telomerase substrates, controls, and primers or ligomers and with DNA ligases or polymerases, the present invention is not so limited. Thus, one can employ ribooligonucleotides or oligonucleotides that comprise one or more modified (i.e., synthetic or non-naturally occurring) nucleotides in the primer extension step. In similar fashion, one can employ an RNA polymerase to extend a primer or to copy an extended telomerase substrate. These and other variations of the present method will be apparent to those of skill in the art upon consideration of this description of the invention.

Regardless of the nature of the primer extension reaction, the various reagents can be labelled to facilitate identification of telomerase-extended telomerase substrates in a reaction mixture. Those of skill in the art will note that while the method of the invention involves the correlation of telomerase activity in a sample with the formation (presence in the reaction mixture) of duplex nucleic acids composed of extended telomerase substrates annealed to extended primers, one can infer the presence of such molecules by the presence of either (1) an extended telomerase substrate; (2) an extended primer; or (3) a duplex nucleic acid comprising both (1) and (2). In any event, however, one will typically make this correlation by detecting the presence of extended telomerase substrates and/or primers via a label incorporated into one or more of the reaction products.

For instance, one can use a labelled nucleoside triphosphate, a labelled primer, or a labelled telomerase substrate (or a combination of the same) and monitor incorporation of the label into telomerase substrate or primer extension products. The control can also be labelled with the same or a different label. Any of a wide variety of labels can be used for purposes of the present invention. Such labels typically include fluorescent, phosphorescent, chemiluminescent, and radioactive labels. Alternatively, the label can merely be an unlabelled "tag", which in turn is recognized by a labelled molecule that binds to the tag. For instance, one can use biotin as the tag, use avidinylated horseradish peroxidase ("HRP") to bind to the tag, and then use a chromogenic substrate (i.e., TMB) to detect the presence of the HRP. In similar fashion, the tag can be an epitope or antigen, and a fluorescently- or radioactively-labelled antibody can be used to bind to the tag.

Detection of the label may involve additional steps, depending on the needs of the practitioner and the particular label or detection means employed. In some instances, the practitioner may first separate reaction products from one another using gel electrophoresis, as exemplified below. Other separation methods, i.e., chromatography, can also be employed, but for some purposes, no separation will be performed, and the detection of extended telomerase substrates and/or primers will be carried out without removing the reaction mixture from the vessel in which the reaction was performed. One important advantage of the present invention is the adaptability of the method to any detection format of interest.

Having this description of the method and reagents employed, one can consider applications for the telomerase assay of the present invention, which include research and diagnostic applications. Because the assay is fast, simple, and amenable to single-tube reactions and in situ detection, the assay can be used in research and clinical laboratory settings where there is a need to detect telomerase-positive cells. Such applications include, but are not limited to: (i) detection of immortal cells in tumor biopsies for the identification of potential cancer cells; (ii) identification in a cell-based or cell-free screen of agents capable of activating, derepressing, inhibiting, or repressing telomerase, including immortalizing agents (e.g., oncogenes) or compounds that might activate telomerase and extend telomeres and replicative lifespan of cells; (iii) identification in culture systems or in vivo of stem cells or early progenitor cells that possess telomerase activity; (iv) examination of telomerase regulation during differentiation and development; (v) identification of telomerase-positive fractions generated during purification of telomerase; (vi) identification of protozoal or fungal infections; and (vii) diagnosis of certain types of infertility characterized by an absence of telomerase activity.

The diagnostic methods of the present invention can be employed with any cell or tissue type of any origin and can be used to detect an immortal cell of any origin, provided the cell expresses telomerase activity. For human samples, the detection of immortal cells will typically be used to detect the presence of cancer cells of any of a wide variety of types, including without limitation, solid tumors and leukemias including: apudoma, choristoma, branchioma, malignant carcinoid syndrome, carcinoid heart disease, carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell), histiocytic disorders, leukemia (e.g., B-cell, mixed-cell, null-cell, T-cell, T-cell chronic, HTLV-II-associated, lymphocytic acute, lymphocytic chronic, mast-cell, and myeloid), histiocytosis malignant, Hodgkin's disease, immunoproliferative small, non-Hodgkin's lymphoma, plasmacytoma, reticuloendotheliosis, metanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing's, experimental, Kaposi's, and mast-cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia.

In the diagnostic methods of the invention, the assay will be conducted to determine whether an elevated level of telomerase is present. The phrase "elevated level" means that the absolute level of telomerase activity in the particular cell is elevated compared to normal somatic cells in that individual, or compared to normal somatic cells in other individuals not suffering from a disease condition. Generally, any detectable level of telomerase activity is considered elevated in cells from normal, post-natal human somatic tissue. Although telomerase activity is present in germline cells, and low levels of telomerase activity can be detected in stem cells and certain hematopoietic system cells, such cells do not present problems for the practitioner of the present method. Germline cells can be readily distinguished and/or separated from human somatic tissue samples, and the telomerase activity present in stem cells and certain hematopoietic cells is present at such low levels that the few such cells present in somatic tissue samples will not create false positive signals from a telomerase activity assay. The detection of telomerase activity in somatic cells is indicative of the presence of immortal cells, such as certain types of cancer cells, and can be used to make that determination even when the cells would be classified as non-cancerous by pathology. Thus, the method of the present invention allows cancerous conditions to be detected with increased confidence before cells become visibly cancerous, Those of skill in the art will also recognize that while the use of cell extracts is preferred for most purposes, one can also modify the method so that intact cells can be employed. In this embodiment, one treats intact cells with the telomerase substrate oligonucleotide, following which the oligonucleotide will be extended if the cell possesses functional telomerase activity. Established in situ PCR and LCR technology with a polymerase or ligase, a primer, and nucleoside triphosphates (if a polymerase is employed) are then used on fixed cells to amplify telomerase-extended substrate oligonucleotides. Telomerase positive cells can then be detected by microscopy utilizing, e.g., incorporation of a labelled nucleotide or oligonucleotide during primer extension.

The diagnostic tests of the invention can also be carried out in conjunction with other diagnostic tests. In some instances, such combination tests can provide useful information regarding the progression of a disease, although the present method for testing for telomerase activity provides much useful information in this regard. When the present method is used to detect the presence of cancer cells in a patient sample, the presence of telomerase activity can be used to determine where a patient is at in the course of progression of the disease, whether a particular tumor is likely to invade adjoining tissue or metastasize to a distant location, and whether an occurrence of cancer is likely to recur. Tests that may provide additional information in conjunction with the present method include diagnostic tests for the estrogen receptor, progesterone receptor, DNA ploidy, fraction of cells in S-phase, nodal status, Her-2/neu gene products, p53, p16, p21, ras, and other oncogenes.

The present invention also provides kits for performing the diagnostic method of the invention. Such kits can be prepared from readily available materials and reagents and can come in a variety of embodiments. For example, such kits can comprise any one or more of the following materials: reaction tubes, buffers, detergent, oligonucleotide telomerase substrates, control reagents, oligonucleotide primers, and instructions. An especially preferred kit of the invention comprises a reaction tube in which is placed a telomerase substrate and a primer. A preferred form of this kit comprises such a tube in which the primer is separated from other reaction components by a wax barrier. A wide variety of kits and components can be prepared according to the present invention, depending upon the intended user of the kit and the particular needs of the user.

The following examples describe specific aspects of the invention to illustrate the invention and provide a description of the present method for those of skill in the art. The examples should not be construed as limiting the invention, as the examples merely provide specific methodology useful in understanding and practice of the invention.

EXAMPLE 1

Preparation of CHAPS-extracted Telomerase

In this Example, cell extracts prepared using the zwitterionic detergent-based extraction method of the invention were tested for telomerase activity using the conventional telomerase assay.

The cell extracts were prepared from immortal 293 cells, which are known to express telomerase activity and are derived from human embryonic kidney cells transformed with fragments of adenovirus type 5 DNA. The cells were grown in Joklik's medium containing 5% to 10% fetal bovine serum and then collected by centrifugation (unless otherwise noted, the procedure below assumes that about $1\times10^6$ cells were collected), washed once in PBS, pelleted at 10,000×g for 1 min. at 4° C., and resuspended in 1 mL of ice-cold wash buffer [10 mM HEPES-KOH (pH 7.5), 1.5 mM $MgCl_2$, 10 mM KCl, 1 mM DTT, DEPC-treated water]. The cells were pelleted again and resuspended in ice-cold lysis buffer [10 mM Tris-HCl (pH 7.5), 1 mM $MgCl_2$, 1 mM EGTA, 0.1 mM PMSF, 5 mM β-mercaptoethanol, DEPC-treated water, 0.5% CHAPS (from Pierce), 10% glycerol] at a concentration of 20 μl of lysis buffer per $10^4$–$10^6$ cells (depending on the purpose of the experiment). The suspension was incubated on ice for 30 min. and then spun in a microultracentrifuge at 100,000×g for 30 min. at 4° C. The supernatant was removed to another tube, quick-frozen on dry ice, and stored at −70° C. These extracts typically contained a total protein concentration of 5 to 10 mg/ml, and the telomerase activity was stable to multiple freeze-thaws.

The procedure for and conditions of the conventional telomerase assay were as described by Counter et al., 1992; Counter et al., 1994, EMBO J. 11:1921–1929; and Counter et al., 1994, *J. Virol.* 68:3410–3414, using oligonucleotide substrates at a concentration of 1 μM. See also Morin, 1989, *Cell* 59:521–529. The products were separated on an 8% polyacrylamide sequencing gel and exposed overnight to a Phosphorimager™ screen (Molecular Dynamics, Sunnyvale, Calif.). The results are shown in FIG. 1, part A. Note that product resolution differs between FIG. 1, part A, and FIG. 2, part B, because of different gel dimensions. The telomerase substrates used in the conventional assay were 5'-GTTAGGGTTAG GGTTAGG-3' (abbreviated as "(GTTAGG)₃" (SEQ ID NO:8); see lane 1 of FIG. 1, part A); 5'-TTAGGGTTAGGGTTAGGG -3' (abbreviated as "(TTAGGG)₃" (SEQ ID NO.9); see lanes 2 and 3 of FIG. 1, part A), and 5'-AATCCGTCGAGCAGAGTT-3' (abbreviated as "TS" (SEQ ID NO.1); see lanes 4 and 5 of FIG. 1, part A). The extracts used in lanes 3 and 5 of FIG. 1, part A, were pretreated with RNase by incubation of 10 μl of extract with 0.5 μg of RNase (DNase-free, Boehringer Mannheim) for 10 min. at 25° C., which degrades the RNA component of telomerase and abolishes activity. Telomerase pauses after adding the first G of the G triplet, so the number of nucleotides added before the first pause (and thus the phasing of the ladder) is five for (GTTAGG)₃ (SEQ ID NO.1) (lane 1), four for (TTAGGG)₃ (SEQ ID NO.9) (lane 2), and two for the TS oligonucleotide (SEQ ID NO.1) (lane 4; see FIG. 1, part B, for a diagram of the TS extension products).

As demonstrated by FIG. 1, part A, the CHAPS-extracted telomerase activity functioned as predicted for human telomerase. The material produced the predicted banding pattern with each of the different telomerase substrates employed, and the banding pattern was abolished with pretreatment of the extract with RNase.

EXAMPLE 2

PCR Amplification of Telomerase Extension Products

This example illustrates the telomerase assay method of the present invention in which a DNA polymerase is used to mediate the primer extension reaction in a polymerase chain reaction. As shown in FIG. 1, part B, the reaction components include the telomerase substrate TS (the sequence of which is provided in Example 1, above), which telomerase extends by synthesizing telomeric repeats (shown by lower case sequence in FIG. 1, part B) and which also functions as the upstream primer in the PCR step, and the downstream primer CX, the structure of which is defined by its sequence 5'-(CCCTTA)₃CCCTAA-3' (SEQ ID NO.2). DNA synthesis during PCR is represented by broken arrows in FIG. 1, part B, and optimal annealing of the CX primer (SEQ ID NO.2) is shown using vertical lines, while asterisks indicate designed mismatches in the CX primer (SEQ ID NO2)/ extended telomerase substrate, which reduce interaction between the CX primer (SEQ ID NO.2) and unextended TS (SEQ ID NO.1) oligonucleotide telomerase substrate and so minimize primer-dimer (more accurately CX primer/TS dimer formation).

As noted above, telomerase is known to extend oligonucleotides of non-telomeric sequence, such as the TS oligonucleotide (SEQ ID NO.1) (Morin, 1991, *Nature* 353:454–456), and oligonucleotide substrate TS was used to avoid non-specific amplification due to PCR primer complementarity. As further modifications to avoid primer interaction, mismatches in the downstream primer CX (SEQ ID NO.2), single stranded binding protein T4 gene 32 protein, hot start PCR, and an annealing temperature of 50° C. were used to conduct the telomerase activity assays described in this Example. Under these conditions, specific amplification occurs only if the oligonucleotide substrate has been extended with three or more 5'-TTAGGG-3' (SEQ ID NO:9) repeats, resulting in a six nucleotide ladder of TRAP assay products extending from 40 nucleotides (the first amplifiable telomerase product) up to the limit of gel resolution.

Yet another important modification that greatly improves the ease and efficiency of the present method relates to the development of a novel reaction buffer in which both telomerase and DNA polymerase can function. Use of this buffer allows one to employ a single tube set-up or format for the TRAP assay, as shown in FIG. 1, part C. This modification allows one to increase the specificity of primer extension, because the CX primer (SEQ ID NO.2) is initially separated from the rest of the reaction mix by a wax barrier, which melts only at the higher temperatures that mediate stringent hybridization conditions. The assay tubes were prepared by adding 2 μl of a 50 ng/μl suspension of CX primer (0.1 μg) (SEQ ID NO.2), which was spun to the bottom of the tube and evaporated until dry in a Speed-Vac™ centrifuge.

A trace amount of bromophenol blue was added to the CX primer (SEQ ID NO.2) suspension to monitor possible leakage through the wax barrier prior to thermal cycling. While the addition of dye for this purpose is in no way required for practice of the present invention, dye addition can be a convenient method for monitoring the integrity of a manufacturing process. Tubes were then heated at 70° C., and 7–10 μl of molten wax (AMPLIWAX™, Perkin-Elmer) was pipetted into the tube. After the wax was allowed to solidify at room temperature, the tubes were stored at 4° C. Tubes were warmed to room temperature before use. No effect on assay performance was observed using prepared tubes stored at 4° C. for up to two months; the expected shelf-life of such tubes (and kits comprising the same) is expected to be at least a year, even at ambient temperatures.

Reactions were typically carried out by the addition of 50 μl of TRAP reaction solution above the wax barrier. The reaction solution contained 20 mM Tris-HCl, pH 8.3, 1.5 mM MgCl$_2$, 63 mM KCl, 0.005% Tween 20, 1 mM EGTA, 50 μM each dNTP, 0.1 μg of TS oligonucleotide (SEQ ID NO.1), 0.5 mM T4 gene 32 protein (1 μg), 0.1 mg/ml BSA, 2 Units of Taq DNA polymerase (optionally use 2 Units of Taq treated with an equal volume of TAQSTART™ antibody from Clontech to enforce hot start PCR), and 1–2 μl of a CHAPS cell extract. For radiolabeling of products, 0.2 to 0.4 μl of 10 μCi/μl α-$^{32}$PdGTP and/or α-$^{32}$PdCTP (3000 Ci/mmol) was added to the reaction. After 10 min. at 20° C. for extension of oligonucleotide TS (SEQ ID NO.1) by telomerase, the tubes were transferred to the thermal cycler (96 well Singleblock™ system, Ericomp) for 27 cycles, each cycle comprising incubation temperatures and periods of 94° C. for 30 sec., 50° C. for 30 sec., and 72° C. for 30 sec. to 1.5 min. The CX primer (SEQ ID NO.2) (0.1 μg) was liberated when the wax barrier melted at ~70° C. Those of skill in the art will recognize that the reaction times, temperatures, and buffers described in this Example can vary, depending upon the needs of the practitioner, the particular substrates and primers employed, and the source of the extract and DNA polymerase.

For instance, the telomerase extension reaction can be conducted at temperatures ranging from about 10 to about 42° C., depending upon the source of the telomerase. The telomerase reaction time can vary widely, depending upon the number of primer extension steps employed, the amount of telomerase expected to be in the sample, and the time available to the practitioner. Typically, the telomerase reaction time will be between 5 and 60 min., but the time could be up to several hours. In similar fashion, the PCR cycles can be composed of cycle times and temperatures that vary widely. The simplest PCR cycle comprises a duplex nucleic acid denaturation step followed by a primer annealing and extension step. While denaturation is typically carried out by heating the reaction mixture, other methods, such as helicase treatment, can be used, and the heating method itself can be conducted at a wide range of temperature for any amount of time sufficient to denature but not damage the DNA. In similar fashion, the time and temperature of the primer annealing step depends to a great extent on the reaction buffer and primer sequence, concentration, and composition, as well as the specificity required by the practitioner, while the time and temperature of the primer extension step depends greatly upon the type of DNA polymerase employed. Those of skill in the art will recognize and understand that the present invention is not limited by the times, temperatures, and variations in buffer and other reaction components that can be employed in the method.

For analysis of the samples, one half of the reaction mixture was analyzed by electrophoresis in 0.5×TBE on 15% polyacrylamide non-denaturing gels. Visualization of the products was by ethidium bromide staining, silver staining, autoradiography, or PHOSPHORIMAGER™ analysis (Molecular Dynamics, Sunnyvale, Calif.) of the gels. The results of the first set of assays described in this Example are shown in FIG. 1, part D. The set of assays was designed to test the specificity of the TRAP assay for telomerase activity.

Lane 1 of FIG. 1, part D, contains a control sample from which the TS oligonucleotide was omitted; lane 2 contains a control sample from which the cell extract was omitted; lane 3 contains a TRAP assay sample of an immortal 293 cell extract; lane 4 contains a sample of 293 extract pretreated by incubation for 10 min. at 65° C. to heat-inactivate the telomerase; lane 5 contains a sample of 293 extract pretreated by incubation for 10 min. with 0.5 μg of RNase (DNase-free, Boehringer Mannheim) at 25° C. to destroy the RNA component of telomerase; lane 6 contains a sample of phenol-extracted 293 extract (by mixing in an equal volume of a 1:1 phenol:chloroform mixture, vortexing for 30 sec., centrifuging to separate the phases, and collecting the aqueous phase); lane 7 contains a sample of 293 extract pretreated with protease by incubation of the extract (50 μl) with 5 μg of Bromelain protease (Boehringer Mannheim) for 10 min. at 37° C., removal of the Bromelin protease by incubation with an equal volume of carrier-fixed α₂-macroglobulin (Boehringer Mannheim) for 30 min. at 25° C. with shaking and then centrifugation (to pellet the α₂-macroglobulin/Bromelain complex) for 10 min. at 10,000×g, and collection of the supernatant for analysis; lane 8 contains a normal fibroblast BJ cell extract, which should lack telomerase activity; lane 9 contains a cell extract enriched for telomerase by DEAE chromatography (Morin, 1991, *Nature* 353:454–456).

AS illustrated in FIG. 1, part D, the results of these multiple control experiments demonstrate that a positive signal in the TRAP assay requires a ribonucleoprotein in an immortal cell extract capable of extending the TS oligonucleotide (SEQ ID NO.2) with two or more 5'-TTAGGG-3' repeats, validating the assay for specific detection of telomerase activity.

To examine more closely the sensitivity of the TRAP assay, another set of assays was conducted to test the limits of detergent extraction and TRAP detection under the conditions employed. For extraction of different numbers of cells, the volume of lysis buffer was kept constant at 100 μl. The results of these assays are shown in FIG. 1, part E. Lane 1 shows the results of assaying about $10^5$ cell equivalents from an extract of $10^7$ normal fibroblast BJ cells; no activity was observed, as indicated by the absence of the ladder of bands. Lane 2 shows the results of assaying about $10^4$ cell equivalents from an extract of $10^6$ immortal 293 cells; telomerase activity was observed. Lane 3 shows the results of assaying about $10^3$ cell equivalents from an extract of $10^5$ 293 cells; telomerase activity was observed. Lane 4 shows the results of assaying about $10^2$ cell equivalents from an extract of $10^4$ 293 cells; telomerase activity was observed. Lane 5 shows the results of assaying about 10 cell equivalents from an extract of $10^3$ 293 cells; no activity was observed. Lane 6 shows the results of assaying a control with lysis buffer only; no activity was observed.

The limit of telomerase detection in $10^2$ cells was confirmed by TRAP assays of serial dilutions of an extract from $10^4$ 293 cells. This limit is a function of the TRAP assay conditions employed and should be considered a practical limit under the given set of conditions rather than an absolute limit of the sensitivity of the current method. For instance, use of primers CTR3 [(5'-CCCTAA-3')₃] (SEQ ID NO.10) or CTR4 [(5'-CCCTAA-3')₄] (SEQ ID NO.11) instead of CX (SEQ ID NO.2) further increases sensitivity, although these primers are more likely to interact with the unextended TS primer (SEQ ID NO.1). The limit of sensitivity was also analyzed by titration of the synthetic telomerase product TS+4 (which contains oligonucleotide TS (SEQ ID NO.1) followed by four telomeric repeats). Dilutions of TS+4 oligonucleotide were mixed with heat-treated (telomerase inactivated) 293 extract and analyzed in TRAP assays. In this analysis, the assay gave a clear positive signal from $10^6$ molecules of TS+4. In addition, telomerase activity from mouse tissue (telomerase activity is present in somatic cells of mice) and cell extracts was detected by TRAP assay even though the mouse telomerase by conventional assay was shown to be mostly non-processive (i.e., adds only a single repeat; Prowse et al., 1993, *Proc. Natl. Acad. Sci. USA* 90:1493–1497), indicating that the TRAP assay is detecting very low levels of processire mouse telomerase activity that cannot be visualized by the conventional assay.

For the convenience of the practitioner, the following product information is provided. Reaction tubes were 0.2 ml Strip-ease™ tubes from Robbins Scientific (Sunnyvale, Calif.) and were autoclaved before use. All oligodeoxyribonucleotides were Ultrapure grade (HPLC-purified) obtained from Keystone Laboratory (Menlo Park, Calif.) and were suspended in DEPC-treated $H_2O$ at a concentration of 1 mg/ml. Taq DNA polymerase, Tween 20, and T4 gene 32 protein were purchased from Boehringer Mannheim. Radioisotopes were purchased from NEN-Dupont. The dNTPs were purchased from Pharmacia and were aliquoted, stored at –20° C., and thawed (no more than twice) before use. All other reaction components were molecular biology grade and purchased from Sigma, except when otherwise noted. Diethylpyrocarbonate (DEPC)-treated, de-ionized, sterile $H_2O$ was used routinely.

EXAMPLE 3

Relative Sensitivity of TRAP and Conventional Telomerase Assays—Assay of Telomerase Activity in Normal Somatic and Immortal Cells This Example describes telomerase assays conducted on cell samples of immortal cell lines and normal somatic cell cultures. Adherent cell cultures, such as BJ cells, a normal somatic cell culture of human skin fibroblasts, were grown to 80% confluency prior to extract preparation. The assays ($10^5$ cell equivalents per reaction) were conducted as described in Examples 1 and 2, above, and the results of the assay are shown in FIG. 2, parts A and B, and in Table 1, below. The TRAP assay results are shown in FIG. 2, part A; and the conventional assay results are shown in FIG. 2, part B. Assays were performed on the same 10 cell extracts, which were prepared using the CHAPS detergent lysis method (see Examples 1 and 2, above).

In FIG. 2, part A, the even-numbered lanes show the results for extracts pretreated with RNase, which should eliminate any telomerase activity in the sample. Lanes 1 and 2 show the results for breast carcinoma line MCF-7/ADR-RES; lanes 3 and 4 show the results for pancreatic carcinoma line AsPC-1; lanes 5 and 6 show the results for prostatic carcinoma line PC-3; lanes 7 and 8 show the results for melanoma line M14; lanes 9 and 10 show the results for normal foreskin fibroblast cell culture BJ; lanes 11 and 12 show the results for lung carcinoma line NCI-H23; lanes 13 and 14 show the results for normal stromal fibroblast cell culture 31YO; lanes 15 and 16 show the results for normal lung fibroblast cell culture IMR-90; lanes 17 and 18 show the results for ovarian carcinoma line OVCAR-3; lanes 19 and 20 show the results for colon carcinoma line COLO205; lanes 21 and 22 show the results for immortal kidney cell line 293. In FIG. 2, part B, the results for the conventional assays ($10^6$ cell equivalents per reaction) are shown. Lane 1 shows the results for immortal cell line 293; lane 2 shows the results for RNase pretreated 293; lanes 3–12 are the same as odd lanes 1–19 in FIG. 2, part A.

Some immortal cell lines (293, MCF-7/ADR- RES, NCI-H23, OVCAR-3, COLO205, M14) show activity in both assays, others (AsPC-1 and PC-3) show activity only in the TRAP assay, and the normal somatic cell cultures (BJ, IMR-90 and 31YO) show no detectable activity by either assay. These results demonstrate that the TRAP method can detect telomerase activity in extracts that test negative by the conventional assay.

This survey was expanded to include a total of 74 immortal cell lines and 22 normal somatic cell cultures from 18 different tissues, and the results are summarized in Table 1, below. Each dividing cell culture was detergent-extracted and tested for telomerase activity using the TRAP assay. The specific immortal cell lines and normal somatic cell cultures are listed by tissue of origin. Immortal cell lines and normal somatic cell cultures tested were: (1) Skin—melanoma (LOXIMVI, M14, Malme-3M, UACC-62), normal fibroblasts (GFS, S37b, Malme-3, BJ), normal keratinocytes (1° foreskin); (2) Connective—Fibrosarcoma (HT-1080); (3) Adipose—liposarcoma (SW872); (4) Breast—adenocarcinoma (MCF7, MCF-7/ADR-RES, MDA-MB-231), ductal carcinoma (T 47 D, MDA-MB-435), carcinoma (MDA-MB-157, MDA-MB-175-VI, MDA-MB-436, MDA-MB-468, ZR-75-1, ZR-75-30, UACC-812, UACC-893, BT-20, BT-474, BT-483, BT-549, HSS78T, SK-BR-3, SCC70, SCC38, SCC202), normal epithelial and stromal cells (HME: 15, 17, 31, 32, 35); (5) Lung—carcinoma (NCI-H522, NCI-H23, A549, EKVK, 1299, H146, H69, NCI-H460, H358, H182), SV40 T-antigen transformed (IDH4, SW26-IG, SW-26-C4), normal fetal fibroblasts (GFL, IMR-90, Wi38); (6) Stomach—gastric carcinoma (KATO-III); (7) Pancreas— ductal carcinoma (SU.86. 86), adenocarcinoma (AsPC-1, Capan-1); (8) Ovary—carcinoma (OVCAR-3, OVCAR-5, IGROV-1), adenocarcinoma (OVCAR-8); (9) Cervix—carcinoma (HeLa S3, C-33 A, HT-3), normal 1° epithelial cells; (10) Uterus—normal 1° endometrial cells; (11) Kidney—carcinoma (A498, CAKI-1), Ad5-transformed embryonic kidney cells (293); (12) Bladder—carcinoma (5637), transitional cell carcinoma (T24), squamous carcinoma (SCaBER), normal fetal (FHs 738B1); (13) Colon—adenocarcinoma (COLO 205, SW-620, HCT-116); (14) Prostate—adenocarcinoma (PC-3, DU 145), SV40 transformed BPH fibroblasts (BPH-1), normal stromal fibroblasts (31YO), BPH fibroblasts (S52); (15) CNS—carcinoma (U251, SNB-75), glioblastoma (SF268); (16) Blood—leukemia (Molt4, HEL), T-cell leukemia (Jurkats), acute promyelocytic leukemia (HL-60), chronic myelogenous leukemia (K-562), histiocytic lymphoma (U-937); (17) Retina—SV40 transformed pigmented epithelium (AGO6096A); and (18) Joint: normal synovial fibroblast (HSF).

TABLE 1

Telomerase Activity in Mortal and Immortal Cells

| Tissue of Origin | Cell Type (Tumor/ Transformed/ Normal/) | Telomerase Activity (# positive/ # tested) |
|---|---|---|
| Skin | Tumor | 4/4 |
|  | Normal | 0/5 |
| Connective | Tumor | 1/1 |
| Joint | Normal | 0/1 |
| Adipose | Tumor | 1/1 |
| Breast | Tumor | 22/22 |
|  | Normal | 0/8 |
| Lung | Tumor | 10/10 |
|  | Transformed | 2/3 |
|  | Normal | 0/3 |
| Stomach | Tumor | 1/1 |
| Pancreas | Tumor | 3/3 |
| Ovary | Tumor | 4/4 |
| Cervix | Tumor | 3/3 |
|  | Normal | 0/1 |
| Uterus | Normal | 0/1 |
| Kidney | Tumor | 2/2 |
|  | Transformed | 1/1 |
| Bladder | Tumor | 3/3 |
|  | Normal | 0/1 |
| Colon | Tumor | 3/3 |
| Prostate | Tumor | 2/2 |
|  | Transformed | 0/1 |
|  | Normal | 0/2 |
| CNS | Tumor | 3/3 |
| Retina | Transformed | 1/1 |
| Blood | Tumor | 6/6 |

None of the normal somatic cell cultures displayed detectable telomerase activity in the TRAP assay. Of the 74 immortal cell lines, 68 were tumor-derived lines and 6 were cell lines transformed with vital oncoproteins. All of the 68 tumor lines contained telomerase activity. Two of the six transformed lines tested negative for telomerase activity. If these two lines are immortal, then the lack of detectable telomerase activity is unexpected. However, an investigation of telomere length in these lines showed that the telomeres were longer than those of the normal somatic cells from which the lines were derived, which may indicate that the cells experienced a transient burst of telomerase activity. If the telomerase activity is not reinitiated, then the cells will not replicate indefinitely.

EXAMPLE 4

Standard Operating Procedure for Telomeric Repeat Amplification Protocol (TRAP)

This Example provides a step-by-step protocol for performing the TRAP assay of the invention, in five parts: (A) Work station set-up; (B) Precautions; (C) Micro-extraction; (D) Quantitative Assay; and (E) Analysis. The method described provides for a quantitative analysis of the activity, and while a number of recommendations are made, those of skill will recognize that, depending on the conditions used and nature of the results desired, not all recommendations need be followed in all circumstances.

A. Work Station Set-up

An important factor in the set-up of the TRAP assay is the environment where the initial reaction mixtures are made prior to the PCR step. The ideal environment is free of contaminating ribonucleases and PCR amplified DNA products, which can cause erroneous negative and positive results, respectively. A major source of PCR product (and RNase) contamination can be the person performing the experiment, who should maintain high standards of personal hygiene and avoid generation of aerosols of PCR products when opening or pipetting PCR products or disposing of gel buffer after the electrophoresis of PCR products. A positive air displacement hood, which blows in filtered air over the sample toward the investigator, is ideal. Separate solutions, pipettes, tubes, and tips should always be used and kept inside the hood. Work space should be wiped with 10% bleach prior to set-up of the reaction, and the hood should be routinely UV-irradiated when not in use. Also, barrels of pipettes should be periodically soaked in 10% bleach, even when aerosol-resistant tips are used. The investigator should wear gloves and a disposable lab coat with elastic wrist straps; the lab coat should be periodically changed.

A dedicated work area for setting up TRAP reaction can be prepared by placing an acrylic shield of 45.7 cm (L)×30.5 cm (W)×61 cm (H) size from VWR (cat. #56615-848) on a standard cubby-hole type desk. The top of the desk is covered either by a board or heavy cloth, and the front is blocked by the shield. This arrangement creates dead-air space, where the contaminants are prevented from falling into the working area from outside and the samples are physically blocked from the investigator. All the solutions, pipettes, tips, and tubes are kept inside the station, and the working area is routinely UV irradiated by a short-wave UV lamp mounted on the top of the station (Black Ray UV lamp, XX-15S, VWR cat#36575-059).

(B) Precautions

As noted above, and because the TRAP assay incorporates both PCR amplification and use of in vitro activity of a ribonucleoprotein (telomerase), there is a need for extreme caution to prevent PCR-product contamination (DNA) and RNase contamination, both of which can be detrimental to the assay. The following basic precautions can be followed in all steps of the assay protocol, including the telomerase extraction and PCR amplification steps, to avoid problems: (1) use DEPC-treated $H_2O$ for all solutions, and aliquot the solutions in small amounts before use; (2) keep the assay solutions (PCR buffer, CHAPS extraction buffers, dNTPs, Taq polymerase, etc.) separate from other reagents in the laboratory; (3) wear gloves; (4) use a dedicated set of pipettors for the assay and aerosol-resistant tips (ARTs); and (5) do not analyze the amplified samples in the same area where the samples are prepared (i.e., do not open PCR tubes after the PCR amplification on the same bench where the assay reagents and pipettes/tips are located; instead use other pipettors (optionally without ARTs) at a location away from the PCR bench).

(C) Micro-extraction

The material requirements for the lysis buffer used in the micro-extraction procedure are shown below.

| Lysis Buffer (0.5% CHAPS* or CHAPSO*) | | | |
|---|---|---|---|
| Stock | Final | 0.5 mL | 10 mL |
| 1 M Tris-HCl pH 7.5 | 10 mM | 5 µl | 100 µl |
| 1 M $MgCl_2$ | 1 mM | 0.5 µl | 10 µl |
| 0.5 M EGTA | 1 mM | 1 µl | 20 µl |
| *0.1 M PMSF | 0.1 mM | 0.5 µl | 10 µl |
| *BME (14.4 M) | 5 mM | 0.17 µl | 3.5 µl |
| 10% Detergent | 0.5% | 25 µl | 500 µl |
| 100% Glycerol | 10% | 50 µl | 1 mL |
| DEPC $H_2O$ | | 417.83 µl | 8.36 mL |

*The CHAPS or CHAPSO detergent should be added just before use of the lysis buffer. In addition, one should add 0.1 M PMSF (1 µl) and beta-mercaptoethanol (0.35 µl) to 1 ml of lysis buffer just prior to performing the extraction step.

The micro-extraction procedure involves the following steps:

1. Establish the cell count, pellet the cells, wash the cells twice in PBS (Ca and Mg—free), repeller, and remove PBS.
2. Suspend cells in wash buffer and repeller the cells.
3. Remove wash buffer, resuspend cell pellet in 20 µl of lysis buffer per $10^6$–$10^4$ cells (depending on the application).
4. Incubate the cells on ice for 30 min.
5. Spin the cells in a microcentrifuge (Eppendorf) at 10000×g for 20 min. at 4° C.
6. Remove extract to another tube, use 1 to 2 µl per TRAP assay; one can quick-freeze the remainder on dry-ice and store at −70° C., if desired.

(D) Quantitative Assay

The following materials are recommended for the assay: TRAP wax-barrier reaction tubes; ACT primer (5'-GCGCGG[CTAACC]$_3$-3' (SEQ ID NO.3), 100 ng/tube); 2.5 mM dNTPs (Pharmacia); end-labeled TS Primer (M2, 0.1 mg/ml) (SEQ ID NO.1); Taq polymerase (Boehringer Mannheim); and 10×TRAP Buffer.

| 10X TRAP Buffer | |
|---|---|
| Components | For 5 ml |
| 200 mM Tris-HCl, pH 8.3 | 1 ml (1 M Tris-Cl pH 8.3) |
| 15 mM $MgCl_2$ | 75 µl (1 M $MgCl_2$) |
| 630 mM KCl | 3.15 ml (1 M KCl) |
| 0.05% Tween 20 | 25 µl (Boehringer Mannheim) |
| 10 mM EGTA | 500 µl (0.1 M EGTA) |
| 1 mg/ml BSA | 250 µl (20 mg/ml) |

| 10X TRAP Buffer | |
|---|---|
| Components | For 5 ml |
| ACT-IC | 0.77 to 1.54 pg (5–10 amol/50 µl reaction mixture) |

ACT-IC is an internal control oligonucleotide of sequence: 5'-AATCCGTCGAGCAGAGTTAGCCCGGT TAGGGTTAGGGTTAGCCGCGC-3' (SEQ ID NO.12), specifically designed for the M2 (TS) (SEQ ID NO.1) telomerase substrate (and PCR primer) and the ACT primer. Note that the presence of the sequence complementary to the anchor sequence is optional, and that it may be desirable in some instances not to have this sequence present in the internal controls. Presence of this oligonucleotide internal control (the final amount of ACT-IC (SEQ ID NO.12) will be 5-to-10 amol [$10^{-3}$ fmol] per 50 µl TRAP reaction) will result in a specific PCR amplification product that appears as a band on a gel between the first and second products of the TRAP assay, regardless of RNase treatment or no-extract control. This internal control band can be used to normalize the PCR amplifications from different samples, and to calculate the number of telomerase products generated when used in combination with end-labeled TS oligonucleotide substrate/primer (SEQ ID NO.1) (see Analysis, below).

To prepare a reaction mixture, the following materials are mixed in the TRAP reaction tube, which contains 0.1 µg of dried ACT primer (SEQ ID NO.3) under a wax barrier.

| Material | For 50 µl Total Volume |
|---|---|
| 10X TRAP Buffer | 5 µl |
| 2.5 mM dNTPs (Pharmacia) | 1 µl |
| *Primer (0.1 mg/ml TS) | 1 µl |
| Taq (Boehringer Mannheim) | 0.4 µl (2 Units) |
| Telomerase Extract | 2 µl |
| $H_2O$ | 40.6 µl |

*For a quantitative TRAP assay, one can end-label the TS substrate/primer (SEQ ID NO. 1) with, e.g., [$^{32}$P]-gamma-ATP using T4 polynucleotide kinase, or with other reagents, such as 5'-biotin, digoxigenin, fluorescein or another fluorophore, depending on the particular detection and quantification system to be employed.

Optional ingredients include 0.2 µl of T4 gene 32 protein (5 mg/ml, available from Boehringer Mannheim), and 0.4 µl of TAQSTART™ antibody (available from Clontech). The reaction is carried out according to the following steps:

1. incubate the reaction mixture at room temperature (20° C.) for 10 min.;
2. incubate the reaction mixture at the following temperatures for the times indicated to conduct the PCR: 94° C./30 sec., 60° C./30 sec., and 72° C./30 sec.; repeat this three-step cycle to conduct 20–30, preferably 27, cycles;
3. add loading dye containing bromophenol blue and xylene cyanol, and subject samples to 10–15% non-denaturing PAGE in 0.6×TBE, until the bromophenol blue runs off the gel (molecular marker V from Boehringer Mannheim is a good DNA marker for this gel); and
4. observe product formation, e.g., by PHOSPHORIMAGER™ screen (for a radioactive label) or another appropriate means of detection.

(E) Analysis

Using the protocol outlined above and assuming that the internal control is amplified with the same efficiency as the telomerase substrate extension products, one can estimate the number of telomerase molecules generated in a given reaction, according to the formula (T=total counts per lane):

[(T TRAP Products—T ACT-IC)/T ACT-IC]×(number of molecules of ACT-IC (SEQ ID NO.12) added)

The resulting number is the number of molecules of telomerase products generated for a given incubation time (usually 10 min.). This calculation is valid only if the TS substrate was end-labeled and does not apply to a TRAP protocol in which direct incorporation of radioactive dNTPs is used for detection (even if the ACT primer (SEQ ID NO.3) and internal controls are utilized). These conditions also account for possible variations in PCR amplification between samples and so provide a standard measurement.

If an extract has high levels of telomerase activity, then the signal from the ACT-IC (SEQ ID NO.12) can be more difficult to detect, because this method involves a "competitive PCR" in which the telomerase products and the internal controls are both competing for the same primers. In other words, the primers should be present in excess over templates for the quantitative analysis to be accurate. Therefore, if a sample has very high levels of telomerase activity, one can dilute the extract so that the PCR primers are not limiting. Alternatively, one can add a control nucleic acid of any sequence to the reaction mixture in known amounts and amplify the control with primers different from those used to amplify the extended telomerase substrate. The control oligonucleotide and/or the primers used to amplify the control oligonucleotide can be labelled identically to or differently from the label used to label the telomerase extension products.

The foregoing examples describe various aspects of the invention and how the method can be practiced. The examples are not intended to provide an exhaustive description of the many different embodiments of the invention. All publications and patent applications cited above are hereby incorporated herein by reference as if each individual publication or patent application were specifically and individually indicated to be incorporated by reference. Thus, although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method for determining whether a cell sample contains telomerase activity, said method comprising the steps of:

(a) preparing a cell extract from said cell sample;

(b) placing an aliquot of said cell extract in a reaction mixture comprising a telomerase substrate lacking a telomeric repeat sequence and a buffer in which telomerase can catalyze extension of said telomerase substrate by addition of telomeric repeat sequences;

(c) adding to said reaction mixture a primer comprising a sequence sufficiently complementary to a telomeric repeat to hybridize specifically thereto under conditions such that if an extended telomerase substrate is present in said reaction mixture, said primer will hybridize to said extended telomerase substrate and extend to form a complementary copy of said extended telomerase substrate, thereby forming duplex DNA molecules comprising an extended telomerase substrate bound to an extended primer; and (d) correlating presence of telomerase activity in said cell sample with presence of duplex DNA molecules comprising an extended telomerase substrate bound to an extended primer and absence of telomerase activity in said cell sample with absence of said duplex DNA molecules.

2. The method of claim 1, wherein step (c) additionally comprises steps of:

(1) heating said reaction mixture to denature said duplex DNA molecules; and (2) cooling said reaction mixture to a temperature at which complementary nucleic acids can hybridize and said primer can extend if extended telomerase substrates are present.

3. The method of claim 2, wherein said heating and cooling steps are repeated at least 5 times, and said primer is present in amounts sufficient for the formation of extended primers during each cooling step.

4. The method of claim 2, wherein a template-dependent DNA polymerase is present in the reaction mixture of step (c) of claim 1 and said primer is extended by addition of nucleotides to said primer by said DNA polymerase.

5. The method of claim 2, wherein a template-dependent DNA ligase is present in the reaction mixture of step (c) of claim 1 and said primer is extended by ligation of an oligonucleotide ligomer to said primer by said DNA ligase.

6. The method of claim 3, wherein a thermostable template-dependent DNA polymerase is present in the reaction mixture of step (c) of claim 1 and said primer is extended by addition of nucleotides to said primer by said DNA polymerase.

7. The method of claim 3, wherein a thermostable template-dependent DNA ligase is present in the reaction mixture of step (c) of claim 1 and said primer is extended by ligation of an oligonucleotide ligomer to said primer by said DNA ligase.

8. The method of claim 3, wherein said cell extract is prepared by lysing cells in said cell sample in a buffer comprising a non-ionic or zwitterionic detergent.

9. The method of claim 3, wherein said cell sample is a human cell sample.

10. The method of claim 3, wherein said primer is initially kept separate from said cell extract by a wax barrier, and said reaction mixture is heated to melt said wax barrier and add said primer to said reaction mixture.

11. The method of claim 3, wherein said reaction mixture comprises a labelled telomerase substrate.

12. The method of claim 3, wherein said reaction mixture comprises a labelled primer.

13. The method of claim 3, wherein said reaction mixture comprises a labelled nucleoside triphosphate.

14. The method of claim 6, wherein said telomerase substrate and said primer have sequences that do not substantially bind to one another to form a dimer of said substrate and said primer during said primer extension step.

15. The method of claim 6, wherein said primer comprises a non-telomeric repeat sequence at a 5'-end of said primer.

16. The method of claim 6, wherein said primer comprises at least 2 telomeric repeat sequences.

17. The method of claim 7, wherein said primer and ligomer are initially kept separate from said cell extract by a wax barrier and said reaction mixture is heated to melt said wax barrier and add said primer and said ligomer to said reaction mixture.

18. The method of claim 9, wherein said telomerase substrate lacking a telomeric repeat sequence is oligonucleotide TS (SEQ ID NO. 1).

19. The method of claim 9, wherein said primer is CX (SEQ ID NO. 2) or ACT (SEQ ID NO. 3).

20. The method of claim 12, wherein said label is selected from the group consisting of a radioactive molecule, a fluorescent molecule, a phosphorescent molecule, a ligand for a receptor, biotin, and avidin.

21. The method of claim 3, wherein said primer of step (c) comprises a sequence at its 5' end that is non-complementary to a telomeric repeat sequence.

22. The method of claim 1, wherein said buffer is a buffer in which a template-dependent DNA polymerase or template-dependent DNA ligase can extend said primer by the addition of nucleotides or oligonucleotide ligomers.

23. The method of claim 22, wherein said buffer is an aqueous solution having about 20 mM Tris-HCl, pH 8.3, 1.5 mM $MgCl_2$, 63 mM KCl, 0.005% Tween 20, and 1 mM EGTA.

* * * * *

UNITED STATES PATENT AND TRADEMARK OFFICE
CERTIFICATE OF CORRECTION

PATENT NO. : 5,629,154
DATED : May 13, 1997
INVENTOR(S) : Nam W. Kim, et al

It is certified that error appears in the above-identified patent and that said Letters Patent is hereby corrected as shown below:

Column 1, Line 48: Delete "replicatire" and insert --replicative--

Column 1, Line 55: Delete "replicatire" and insert --replicative--

Column 2, Line 46: Delete "$10^4$-$10^8$" and insert --$10^7$ to $10^8$--

Column 12, Line 4: Delete "quantirate" and insert --quantitate--

Column 13, Line 1: Delete "Processire" and insert --Processive--

Column 16, Line 7: Delete "metanoma" and insert --melanoma--

Column 19, Line 22: Delete "5'-TTAGGG-$_3$'" and insert --5'-TTAGGG-3'--

Column 21, Line 14: Delete "SEQ ID NO. 2" and insert --SEQ ID NO. 1--

Column 21, Line 39: Delete "$10^4$293" and insert --$10^6$ 293--

Column 23, Line 8: Delete "HSS78T" and insert --HS578T--

Column 27, SEQ ID. NO. 2, after "Linear", Delete "52-B"

Signed and Sealed this

Sixth Day of October, 1998

BRUCE LEHMAN

Attest:

Attesting Officer

Commissioner of Patents and Trademarks